United States Patent [19]

Pedersen et al.

[11] Patent Number: 4,467,012

[45] Date of Patent: Aug. 21, 1984

[54] COMPOSITION FOR ABSORBENT FILM AND METHOD OF PREPARATION

[75] Inventors: Lee C. Pedersen, Delano; Lyle F. Elmquist, St. Paul, both of Minn.

[73] Assignee: Grain Processing Corporation, Muscatine, Iowa

[21] Appl. No.: 503,414

[22] Filed: Jun. 13, 1983

Related U.S. Application Data

[62] Division of Ser. No. 290,385, Aug. 5, 1981, Pat. No. 4,412,036.

[51] Int. Cl.$^3$ ..................... B32B 23/02; B32B 23/08; B32B 27/30
[52] U.S. Cl. .................................... 428/248; 156/180; 156/181; 156/307.1; 156/307.3; 156/307.7; 156/328; 156/331.8; 427/370; 427/392; 428/236; 428/249; 428/264; 428/289; 428/507; 428/508; 428/514; 428/522; 428/534; 428/536; 428/704

[58] Field of Search .................. 523/54.24, 54.26, 105, 523/111; 428/411, 236, 248, 249, 264, 289, 507, 508, 514, 522, 534, 536; 427/370, 392; 156/307.1, 307.7, 180, 181, 307.3, 328, 331.8

[56] References Cited

U.S. PATENT DOCUMENTS 4,282,121  8/1981  Goodrich .......................... 525/54.26

Primary Examiner—Ellis P. Robinson
Attorney, Agent, or Firm—Neuman, Williams, Anderson & Olson

[57] ABSTRACT

An absorbent composition comprising the reaction product at elevated temperature and pressure of hydrolyzed starch polyacrylonitrile graft copolymer and a polyhydric alcohol such as glycerol in the amount of between about 3% and 20%. The resulting composition exhibits good fluid absorbency and fast wicking properties and is particularly useful in producing absorbent laminated film for use in diapers, paper towels and the like. The present invention also relates to an improved absorbent laminated film prepared with the above absorbent composition and a method for preparing such absorbent laminated film.

20 Claims, No Drawings

COMPOSITION FOR ABSORBENT FILM AND METHOD OF PREPARATION

This is a division of application Ser. No. 290,385 filed Aug. 5, 1981, now U.S. Pat. No. 4,412,036.

The present invention relates to an improved absorbent composition and more particularly to an improved absorbent composition prepared by combining hydrolyzed starch polyacrylonitrile graft copolymer and a polyhydric alcohol such as glycerol. The resulting composition exhibits good fluid absorbency and fast wicking properties and is particularly useful in producing laminated absorbent film for use in diapers, paper towels and the like. The present also relates to an absorbent laminated film comprising the above composition as an absorbent layer and a method for preparing the same.

BACKGROUND OF THE INVENTION

There are countless uses for laminated films which exhibit good fluid absorbency as well as fast wicking properties. Such laminated films are useful in the manufacture of diapers, paper towelling, bandages, surgical pads, tissues and the like. Usually a laminated film of this type provides one of the above desired properties but not both. Normal preparation of absorbent laminated films involves making an absorbent water dispersion of the absorbent composition, laying down a thin wet film, drying the same and then applying it to an appropriate tissue layer or layers.

Hydrolyzed starch polyacrylonitrile graft copolymers which exhibit the capacity to absorb from about 300 to 1000 times their weight of deionized water are known at this time. The development of these compositions was carried out by the Northern Regional Research Laboratory at Peoria, Ill. Starch polyacrylonitrile graft copolymer is produced by the free radical method of polymerization. In this method, starch, either gelatinized or ungelatinized, is exposed to a catalyst such as ceric ammonium nitrate which acts as a catalyst to generate free radicals in the starch chain. These free radicals can also be produced by radiation. Polyacrylonitrile chains become attached to these free radicals by copolymerization. A wide range of substitution in these copolymers is known in the art. For example, U.S. Pat. No. 3,035,099 shows a preparation of copolymers in which the starch to polyacrylonitriles molar ratios range from 1:1.5 to 1:9. The variations in molar ratio of the components of the copolymer is not critical to the practice of this invention. The resulting material is then saponified to hydrolyze the polyacrylonitrile chains to carboxy amide and alkali metal carboxylate groups mixed with metal salts. Drying the hydrolyzed material can be accomplished by tumble air drying or vacuum drying. After drying, the material can absorb about 300 to 400 times its weight of deionized water. Washing the absorbent polymer before drying with alcohol increases its absorbency to 800 to 1,000 times its weight of deionized water.

To use this absorbent copolymer as part of a laminated film in such products as towelling, diapers, bandages, surgical pads, tissues, etc. the hydrolyzed starch polyacrylonitrile graft copolymer which is normally in powder form is formed into a thin film. To do this, it is first dispersed in water, then sheared to a small size, layed down as a wet film and finally dried. The resulting product is a thin film of absorbent material which is then applied directly to backing tissues to form a laminated film comprising the backing tissues and the absorbent material. Although this resulting product is generally highly absorbent, the wicking properties are somewhat reduced because of the reduced surface area between adjacent particles of the absorbent polymer and because of blocking caused by the highly absorbent polymer material. Further, the cost of preparing laminated absorbent film in the above manner is quite expensive. Accordingly, there is a need for an absorbent composition usable in the preparation of absorbent laminated film of the type which retains its fast wicking properties as well as its high absorbent characteristics.

SUMMARY OF THE INVENTION

According to the present invention, and in contrast to the prior art, it has been found that by adding a small amount of a polyhydric alcohol such as glycerol to hydrolyzed starch polyacrylonitrile graft copolymer and disposing the same between a pair of backing carriers or backing tissues in the presence of heat and pressure, a desirable laminated film is formed having good fluid absorbency as well as fast wicking properties. It is believed that the increased wicking properties stem from the fact that the absorbent polymer is retained more as individual absorbent particles than as a continuous sheet of film formed in the conventional manner described above. Thus, the surface area of the absorbent composition of the present invention, when disposed between backing tissue sheets to form a laminated film, is significantly increased over the surface area of the absorbent composition layer of absorbent laminated films of the prior art.

Also, unlike the prior art absorbent laminated films which are quite brittle and stiff, the absorbent laminated film prepared with the composition of the present invention and in accordance with the procedure of the present invention is very soft and flexible; an extremely beneficial characteristic when used in the manufacture of towelling, diapers and the like where softness is desirable.

Accordingly, a primary object of the present invention is to provide an absorbent composition which has particular use in the preparation of absorbent laminated film.

Another object of the present invention is to provide an improved absorbent laminated film.

A further object of the present invention is to provide an improved method of preparing an absorbent composition and an absorbent laminated film utilizing such absorbent composition.

These and other objects of the present invention will become apparent with reference to the detailed description of the invention set forth below.

DETAILED DESCRIPTION OF THE INVENTION

The hydrolyzed starch polyacrylonitrile graft copolymers which are the basic absorbent polymers employed in the present invention are well known and commercially available as indicated in the Background of the Invention discussed above. In many of the examples set forth below, the hydrolyzed starch polyacrylonitrile graft copolymer employed is the commercially available product manufactured by Henkel Corporation under the trademark SGP 147. This starch graft polymer is typically a dry powder having high fluid absorbency and good wicking properties. The dry powder is available in varying granulations with the granulation of the material used in the examples below being −30 mesh.

The commercially available product SGP 147 may also be described generally as a polymer comprised of a naturally occurring polymer (starch) and a synthetic polymer (acrylamide and alkali metal acrylate). Proportions of starch and acrylic polymer of the SGP 147 polymer are about 2:3 while proportions of acrylate and acrylamide are about 3:1. It is contemplated that hydrolyzed starch polyacrylonitrile graft copolymers other than the above-mentioned SGP 147 polymer could be employed in the present invention to produce a desired absorbent composition for use in preparing a laminated film. The particular characteristics desired in the end product will dictate which particular starch graft polymer is utilized.

The polyhydric alcohols employed by the present invention are those commonly referred to as the sugar alcohols which bear a close relationship to the simple sugars from which they are formed and from which their names are often derived. These polyols contain straight carbon chains in which each carbon atom bears a hydroxyl group. The sugar alcohols applicable in the present invention are those which can be defined by the general formula:

$$HOCH_2(CHOH)_nCH_2OH$$

where n is 1–5. Included among the above alcohols are glycerol, erythritol, xylitol, sorbitol, mannitol and dulcitol with glycerol being the most preferred or desirable for the purposes of the present invention.

The first step in the preparation of the composition of the present invention is to combine the liquid polyhydric alcohol such as glycerol with the powdered hydrolyzed starch polyacrylonitrile graft copolymer. This combination is then mixed thoroughly. While various amounts of the polyhydric alcohol may be combined with the starch graft polymer, certain practical limits exist for the resulting product to be useful. It has been found that for satisfactory results the amount of polyhydric alcohol should be at least 3% but not more than 20% of the total starch graft polymer/alcohol mixture. If the alcohol content is less than 3%, and thus the starch graft polymer greater than 97% it is believed that insufficient cross-linking occurs. This limits the ability of the composition to adhere to tissue backing when applied under appropriate heat and pressure conditions. It is contemplated that a mixture of 20% alcohol content and 80% starch graft polymer will achieve the benefits of the present invention and result in an absorbent composition usable in preparing an absorbent laminated film. However, the desirability of a particular alcohol content may depend on the manner in which the mixture is applied to the backing layer or carrier when preparing the laminated film. If it is applied with some type of vibratory feeder as in the preferred method of the present invention where the flowability of the mixture is important, the desirable upper limit of alcohol content is about 10%. Compositions with an alcohol content greater than 10% result in a mixture having the consistency of a tacky or sticky powder, thus making application via a vibratory feeder less desirable. With the polyhydric alcohol ranging between 3% and 20%, the starch graft polymer would range between 97% and 80%.

Following the mixing of the polyhydric alcohol and the starch graft polymer, the resulting product is still in powder or granular form. The preferred use of this composition is as an absorbent layer in an absorbent laminated structure. In the preferred procedure, the composition is applied between appropriate backing or carrier layers or sheets and then cured under effective heat and pressure conditions. One way of applying the absorbent composition between the backing or carrier sheets is to sprinkle the powdered or granular absorbent composition onto one surface of a first backing sheet via means such as a vibratory feeder. A second backing or carrier sheet is then overlayed onto the absorbent composition. It is contemplated that various kinds of backing or carrier sheets such as cellulosic or synthetic tissues, urethane foam layers and the like may be usable in preparing the absorbent laminated film of the present invention; however, backing or carrier sheets having a cellulosic fiber base are preferred. It is believed that when the absorbent composition is exposed to effective heat and pressure conditions as described below, the composition adheres to and intertwines with the cellulosic fibers thus holding the backing sheets together to form a single piece of laminated film.

Following the application of the absorbent composition to one of the backing or carrier sheets and the overlayment of the second backing or carrier sheet, the resulting laminate is cured by applying effective heat and pressure to the laminated combination. The pressure can be applied by a platen type press or may also be applied in a conventional laminator by feeding the pair of backing sheets with the absorbing composition disposed therebetween, between a pair of pressure rollers. It is contemplated that the preferred commercial application of the present method would utilize such a roller type application. Although various pressures will result in a satisfactory laminate, depending upon the heat applied and the speed at which the sheets are fed between the rollers, pressures between about 100 pounds per linear inch (p.l.i.) and 200 p.l.i. are preferred when pressure is applied via conventional roller type laminators.

It has been found that under some conditions a certain amount of heat is also desirable for curing the composition so that it adheres to and intertwines with the fibers of the backing or carrier layers. There are many different temperatures and pressures which will result in an acceptable product. In most cases it has been found that the temperature required for curing depends to some extent on the amount of pressure applied and vice versa. As a result of tests conducted on a roller-type laminator it was found that when the pressure was set at the machine maximum of 200 p.l.i., some bonding of the absorbent composition to a pair of backing tissue layers was obtained at ambient conditions (75° F.) with no heat at all. Thus, under these conditions, the test was carried out at ambient or room temperature. As the temperature was increased, the bond between the absorbent composition and the tissue backing was significantly improved. Although ambient or room temperature appears to be sufficient to give some bond at high pressures, a temperature of at least about 100° F. is preferred.

Tests were also conducted to determine the effect of a change in pressure at a constant temperature. In these tests, the rollers were maintained at a temperature of about 200° F. and the pressure was varied from a maximum of 200 p.l.i. down to a minimum of virtually zero. Laminated films prepared under these conditions showed excellent bonding at pressures of between 100 p.l.i. and 200 p.l.i. At a pressure of 50 p.l.i., some bonding still occurred but it was a weak bond. When the pressure was reduced to zero, no bonding whatsoever occurred. Accordingly, it has been found that for desirable results some heat and some pressure is desirable. Preferably, the temperature should be at least about 100° F. and the pressure at least about 50 to 100 p.l.i. on a conventional roller-type laminator. It is contemplated that the maximum temperature would be determined by the characteristics of the absorbent composition and the backing layers. The maximum temperature must be less than a temperature that would break down or destroy the structural characteristics of either the absorbent composition or the backing or carrier sheets. According to the tests described above and as set forth in greater detail in the examples below, it appears that a temperature of 350° F. to 400° F. can be used without danger to the absorbent composition or the backing layers. There would appear to be no limitation with respect to maximum pressure that could be used, although it appears that the minimum pressure should be at least about 50 to 100 p.l.i. in a conventional roller-type laminator.

According to tests set forth in the examples below, the speed at which the laminated sheets are fed through the rollers of a conventional laminator also affect the degree of bonding. It was found that for a given temperature and pressure, as the speed was decreased, the bond became better while as the speed was increased, the bond became weaker. Most of the testing was done with a sheet speed of about 50 feet per minute. As the speed was increased, it was found that the temperature and pressure had to be increased accordingly to continue to achieve good bonding results. At speeds of approximately 300 feet per minute, even maximum temperature and pressure conditions did not result in an acceptable bond. Accordingly, it appears that the maximum speed at which the laminated sheets can be fed through a roller-type laminator is less than 300 feet per minute.

Tests were also conducted in the laboratory. In these tests, however, the pressure was applied with a platen press. Thus, pressure was measured in terms of pounds per square inch (p.s.i.) rather than pounds per linear inch (p.l.i.) as in the roller-type laminator. The results of these tests are set forth in the examples below.

The following are examples showing preparation of the laminated film and the absorbent composition in accordance with the present invention. In such examples, all parts and percentages are by weight unless otherwise indicated.

EXAMPLE 1

SGP 147 water absorbent polymer was thoroughly mixed with 1, 2, 3, 4 and 5% glycerin (based on the weight of polymer). For each of these, a ten inch square section of double tissue was separated and the glycerol treated SGP 147 polymer applied to a surface of one tissue layer with a salt shaker. The second tissue layer was then overlayed over the first and the resulting laminated pressed in a platen press at a temperature of 250° F. and a pressure of 1,885 p.s.i. Laminates prepared with 4% and 5% glycerol treated polymer bonded together well while 3% glycerol treated polymer gave a borderline bond. Polymer treated with 1% and 2% glycerol levels gave poor laminates which did not stick together. Laminates prepared with 4% and 5% glycerol treated polymer showed very good wicking and absorbency properties.

EXAMPLE 2

Tests were also conducted to determine whether substances other than the polyhydric alcohols, when combined with starch graft polymer would give beneficial results. In one test, a ten inch square section of double cellulose fiber tissue was separated and wet with a water atomizer. SGP 147 polymer was then sprinkled on using a salt shaker. The resulting laminate was pressed in a cold platen press at 2500 p.s.i. The laminate stuck together but was soft and tore easily due to the water. Water applied to the laminate wicked in very rapidly. When the laminate was prepared without water, it did not stick together and the polymer was lost. The above test was repeated at temperatures of 250° F. and 340° F. and at a pressure of 1,885 p.s.i. Under these conditions, the laminates stuck together and were fairly dry. but preparations using water still caused problems as the tissue was softened and hard to handle before pressing. In another test, laminates were prepared using polymer treated with 2% and 5% mineral oil. The resulting laminate did not stick together even at higher temperatures and pressures.

EXAMPLE 3

In another example, ten inch square laminates were prepared as in example 1 above using SGP 147 water absorbent polymer treated with 5% glycerol at an application of three grams per square foot. Samples of these laminates (approximately 4 inches square) were tested for free fluid absorbency and absorbency after pressure. These samples were compared with currently existing products including Dow Film Laminate prepared by Dow Chemical Company and SGP 101 film laminate made from a dispersion of SGP 150 polymer and latex emulsion and prepared by Henkel Corporation. Results indicated a superior absorbency for the glycerol treated SGP 147 absorbent polymer both in terms of absorbency as well as wicking properties.

EXAMPLE 4

In a series of tests conducted in a contemplated commercial production environment, a supply of two-ply facial tissue was separated and a mixture of 95% SGP 147 starch graft polymer and 5% glycerol applied between the sheets by a conventional vibratory feeder at the rate of approximately four grams per square foot. These separated sheets with the starch graft polymer/glycerol mixture disposed therebetween were then fed between the rollers of a conventional roller-type laminator. This particular laminator had one heated steel roller and one rubber roller which were capable of generating pressures as high as 200 p.l.i. and temperatures of approximately 350° F. During operation, the various machine parameters were changed. These included the temperature, the roller pressure and the speed at which the tissue was fed between the rollers. The following table summarizes the various operating conditions and the characteristics of the resulting bond.

| Temp. (°F.) | Press. (p l.i.) | Speed (ft/min) | Bond Quality |
| --- | --- | --- | --- |
| 75 (ambient) | 200 | 20 | Fair bond |
| 115 | 200 | 20 | Good bond |
| 150 | 200 | 20 | Good bond |
| 200 | 200 | 20 | Good bond |
| 250 | 200 | 50 | Good bond |
| 300 | 200 | 20 | Good bond |

-continued

| Temp. (°F.) | Press. (p l.i.) | Speed (ft/min) | Bond Quality |
|---|---|---|---|
| 300 | 100 | 20 | Good bond |
| 300 | 50 | 20 | Good bond |
| 300 | 50 | 50 | Good bond |
| 300 | 100 | 50 | Fair bond |
| 300 | 150 | 50 | Good bond |
| 300 | 100 | 75 | Good bond |
| 300 | 150 | 75 | Fair bond |
| 300 | 200 | 40 | Good bond |
| 200 | 200 | 75 | Fair bond |
| 200 | 200 | 100 | Good bond |
| 200 | 200 | 150 | Good bond |
| 200 | 200 | 200 | Fair bond |
| 250 | 200 | 200 | Good bond |
| 300 | 200 | 200 | Poor bond |
| 300 | 200 | 250 | Poor bond |
| 350 | 200 | 250 | Good bond |
| 350 | 200 | 300 | Poor bond |

Although the description of the preferred composition, absorbent laminate film and method has been quite specific, it is contemplated that various changes could be made without deviating from the spirit of the present invention. Accordingly, it is intended that the scope of the present invention be dictated by the claims rather than by the detailed description of the invention.

I claim:

1. An absorbent film comprising at least one backing layer and an absorbent composition secured to said backing layer including the reaction product of hydrolyzed starch polyacrylonitrile graft copolymer and a polyhydric alcohol in which, based upon the total weight of the composition, said hydrolyzed starch polyacrylonitrile graft copolymer is present in an amount of about 80% to 97% by weight and said polyhydric alcohol is present in an amount of about 20% to 3% by weight.

2. The absorbent film of claim 1 wherein the hydrolyzed starch polyacrylonitrile graft copolymer is present in the amount of about 90% to 97% by weight and said polyhydric alcohol is present in an amount of about 10% to 3% by weight.

3. The absorbent film of claim 2 wherein said backing layer includes a cellulosic fiber base.

4. The absorbent film of claim 2 including a second backing layer wherein said absorbent composition is disposed between said backing layers.

5. The absorbent film of claim 4 including the reaction product of said hydrolyzed starch polyacrylonitrile graft copolymer and said polyhydric alcohol at a temperature of at least about 100° F.

6. A method of preparing an absorbent film comprising applying an absorbent composition to a backing layer in which said absorbent composition includes a mixture of hydrolyzed starch polyacrylonitrile graft copolymer and a polyhydric alcohol in which, based upon the total weight of the composition, said hydrolyzed starch polyacrylonitrile graft polymer is present in an amount of about 80% to 97% by weight and said polyhydric alcohol is present in an amount of about 20% to 3% by weight and exposing said backing layer and said absorbent composition to a temperature and pressure sufficient to bond the same together.

7. The method of claim 6 wherein the hydrolyzed starch polyacrylonitrile graft copolymer is present in the amount of about 90% to 97% by weight and said polyhydric alcohol is present in an amount of about 10% to 3% by weight.

8. The method of claim 7 wherein said backing layer and said absorbent composition are exposed to a temperature of at least about 100° F.

9. The method of claim 7 including feeding said backing layer and absorbent composition between a pair of rollers.

10. The method of claim 9 wherein said heat and pressure are applied by said pair of rollers and at least one of said rollers is heated.

11. The method of claim 9 wherein the pressure applied is at least about 50 pounds per linear inch.

12. The method of claim 11 wherein the heat applied is at least about 100° F.

13. The method of claim 12 including feeding said backing layer and absorbent composition between the rollers at a speed no greater than about 350 feet per minute.

14. The method of claim 13 wherein the heat applied is at least about 200° F.

15. The method of claim 13 wherein the heat applied is between 100° F. and 350° F.

16. The method of claim 7 including applying said absorbent composition between a pair of backing layers.

17. The method of claim 16 wherein said backing layers comprise a cellulosic fiber base.

18. The method of claim 17 including feeding said backing layers and absorbent composition between a pair of rollers at a temperature of at least 100° F. and at a pressure of at least 50 pounds per linear inch.

19. The method of claim 7 including applying said absorbent composition at the rate of about four grams per square foot.

20. The method of claim 7 wherein said absorbent composition is applied via a vibratory feeder.

* * * * *